United States Patent
Schwarz et al.

(10) Patent No.: US 7,391,518 B1
(45) Date of Patent: Jun. 24, 2008

(54) DEVICE AND METHOD FOR THE DETERMINATION OF THE QUALITY OF SURFACES

(75) Inventors: Peter Schwarz, Geretsried (DE); Uwe Sperling, Geretsried (DE)

(73) Assignee: BYK-Gardner GmbH, Geretsried (DE)

( * ) Notice: Subject to any disclaimer, the term of this patent is extended or adjusted under 35 U.S.C. 154(b) by 84 days.

(21) Appl. No.: 09/607,827

(22) Filed: Jun. 30, 2000

(30) Foreign Application Priority Data

Jul. 2, 1999 (DE) .............................. 199 30 688

(51) Int. Cl.
*G01N 21/00* (2006.01)
*G01N 21/55* (2006.01)
*G01N 21/47* (2006.01)
*G01B 11/30* (2006.01)

(52) U.S. Cl. .................... 356/446; 356/73; 356/445; 356/600

(58) Field of Classification Search ................ 250/559.01–559.12; 356/402, 600–613, 356/403, 405, 406, 416, 418–423, 425, 445–448, 356/239.1, 239.7, 237.2, 73
See application file for complete search history.

(56) References Cited

U.S. PATENT DOCUMENTS

| | | | | |
|---|---|---|---|---|
| 3,580,683 A | * | 5/1971 | Schulkind | 356/414 |
| 3,971,956 A | * | 7/1976 | Jakeman et al. | 250/559.16 |
| 3,999,864 A | * | 12/1976 | Mutter | 356/448 |
| 4,150,898 A | * | 4/1979 | Suga | 356/405 |
| 4,578,959 A | * | 4/1986 | Alsenz | 62/140 |
| 4,602,281 A | * | 7/1986 | Nagasaki et al. | 348/69 |
| 4,676,653 A | * | 6/1987 | Strohmeier et al. | 356/446 |
| 4,750,140 A | * | 6/1988 | Asano et al. | 382/108 |
| 4,838,697 A | * | 6/1989 | Kurandt | 356/406 |
| 4,917,495 A | * | 4/1990 | Steenhoek | 356/328 |
| 4,918,321 A | * | 4/1990 | Klenk et al. | 250/559.05 |
| 4,989,984 A | * | 2/1991 | Salinger | 356/445 |

(Continued)

FOREIGN PATENT DOCUMENTS

DE 19525566 A1 * 1/1997

(Continued)

*Primary Examiner*—L. G. Lauchman
*Assistant Examiner*—Gordon J Stock, Jr.
(74) *Attorney, Agent, or Firm*—Ohlandt, Greeley, Ruggiero & Perle L.L.P.

(57) ABSTRACT

The present invention relates to a device and method for making quantified determinations of the quality of surfaces and wherein the device comprises an optical system with a first optical means and a second optical means as well as a control and evaluation means and an output (display) means. Said first optical means comprises an illuminating means having at least one LED as its light source and serves the function of illuminating the measurement surface at a predetermined angle. Said second optical means is likewise directed at a predetermined angle to the measurement surface and receives the reflected light. A photo sensor of said second optical means emits an electrical measurement signal which is characteristic of said reflected light.

The light emitted from the illuminating means is configured such that its spectral characteristic comprises blue, green and red spectral components in the visible light spectrum. A filter means is arranged in the path of radiation between the light source and the photo sensor and which changes the spectral characteristics of the incident light so as to approach a predetermined spectral distribution. The control and evaluation means control the measurement sequence and evaluate the reflected light, deriving therefrom at least one parameter which is characteristic of the surface.

25 Claims, 6 Drawing Sheets

U.S. PATENT DOCUMENTS

| | | | | |
|---|---|---|---|---|
| 5,000,569 A * | 3/1991 | Nylund | ............ | 356/237.1 |
| 5,155,558 A * | 10/1992 | Tannenbaum et al. | ...... | 356/446 |
| 5,268,749 A * | 12/1993 | Weber et al. | ............ | 356/446 |
| 5,377,000 A * | 12/1994 | Berends | ............ | 356/73 |
| 5,392,125 A * | 2/1995 | Reisser | ............ | 356/445 |
| 5,592,294 A * | 1/1997 | Ota et al. | ............ | 356/402 |
| 5,596,412 A * | 1/1997 | Lex | ............ | 356/613 |
| 5,619,427 A * | 4/1997 | Ohkubo | ............ | 358/523 |
| 5,686,731 A * | 11/1997 | Wiles et al. | ............ | 250/559.22 |
| 5,708,506 A * | 1/1998 | Birang | ............ | 356/600 |
| 5,795,798 A * | 8/1998 | Mishra et al. | ............ | 356/73 |
| 5,867,276 A * | 2/1999 | McNeil et al. | ............ | 356/445 |
| 5,880,826 A * | 3/1999 | Jung et al. | ............ | 356/445 |
| 5,923,434 A * | 7/1999 | Lex | ............ | 600/431 |
| 6,163,038 A * | 12/2000 | Chen et al. | ............ | 257/103 |
| 6,241,672 B1 * | 6/2001 | Hochman et al. | ............ | 359/571 |
| 6,262,845 B1 * | 7/2001 | Sweatt | ............ | 358/514 |
| 6,313,917 B1 * | 11/2001 | Tang et al. | ............ | 356/402 |
| 6,332,573 B1 * | 12/2001 | Gu et al. | ............ | 235/462.06 |
| 6,381,020 B1 * | 4/2002 | Tsukamoto et al. | ........ | 356/445 |
| 6,407,830 B1 * | 6/2002 | Keithley et al. | ............ | 358/514 |
| 6,542,248 B1 * | 4/2003 | Schwarz | ............ | 356/600 |
| 6,631,000 B1 * | 10/2003 | Schwarz | ............ | 356/445 |
| 6,842,250 B2 * | 1/2005 | Schwarz | ............ | 356/445 |
| 6,975,404 B2 * | 12/2005 | Schwarz | ............ | 356/446 |
| 7,006,229 B2 * | 2/2006 | Sperling et al. | ............ | 356/445 |
| 7,027,160 B2 * | 4/2006 | Sperling | ............ | 356/446 |
| 2005/0030542 A1 * | 2/2005 | Schwarz | ............ | 356/445 |

FOREIGN PATENT DOCUMENTS

DE            19628250 A1 *   1/1997

* cited by examiner

DEVICE AND METHOD FOR THE DETERMINATION OF THE QUALITY OF SURFACES

FIELD OF THE INVENTION

The present invention relates to a device and method for determining the quality of surfaces, respectively visual properties of surfaces.

DESCRIPTION OF RELATED ART

The quality of a surface, respectively its visual properties, is to be understood as those physical characteristics which determine the appearance of the surface for a human observer. The characteristics which in particular distinguish the quality of a surface include gloss, haze, distinction of image (DOI), color brightness, surface texture and surface ripples (orange peel), etc.

These parameters constitute important criteria involved in the determination of the quality of a surface such as, for example, the quality of finished, synthetic or metallic surfaces, since the nature of visible surface properties is a decisive characteristic for the overall appearance in numerous technical components and products. A typical example of products of this kind are automobile bodies; the structure and the consistency of the surface plays a crucial role in the visual appearance of such products. In the following, the technical problems which arise in designing surfaces within the realm of automobile technology and with respect to making measured technical assessments based on surface gloss will be explained in greater detail without, however, in any way restricting the present invention as regards its scope of application.

Automobile bodies are customarily provided with a high gloss or metallic finish which has far superior reflective or glossy characteristics than the corresponding values of other surfaces such as, for example, furniture. Such circumstances necessitate an extraordinarily precise preparation of the surfaces to be finished and an especially high degree of attentiveness when applying the finish. Automobile manufacturers today employ a large number of inspectors and make use of many high-priced industrial-sized measuring apparatuses to visually or automatically inspect surface quality in order to distinguish surface quality deficiencies while still at the production stage.

The ISO 2813, $3^{rd}$ edition 1994, stipulates certain standards and testing operations for the regulating of surface gloss which are to serve in ensuring uniform and reproducible measurement methods when determining gloss.

In accordance with the standard, the surface to be examined is to be illuminated with light having a spectral distribution in accordance with the C light type standard of the CIE (Commission Internationale de l' Éclairage). The C light type standard, also known as "daylight," exhibits a color temperature of 6500 K and a continuous wavelength progression through the spectral radiation bandwidth in the visible spectrum range.

The human eye makes use of retinal rods for its so-called "night vision" and three different types of retinal cones for its so-called "day vision" which exhibit spectrally different and overlapping sensitivity curves (cf. D. B. Judd; "Color Perceptions of Deuteranopic and Protanopic Observers", J. opt. Soc. Amer., 39, 252-256, 1949).

Compact portable measuring devices and systems presently available, for example those used in determining surface gloss, usually employ conventional or halogen light bulbs as their light sources. A disadvantage with using such light sources is that the filament ages and part of it vaporizes, whereby the vaporized material characteristically builds up deposits on the inside of the filament's surrounding glass body. As a result, the spectral emission of the filament and the spectral transmitting distribution of the glass body changes over time.

The spectrum radiated by the light bulb is subject to aging.

A further disadvantage of such conventional light sources is that the position of the filament can change over time due to the effects of aging or due to jarring impacts to the device. Thus, frequent recalibrations must be performed on such a measuring device in order to continually ensure the attaining of usable results. A correction of the spectral distribution caused by deposits on the inside of the light bulb's glass body is only possible, however, by replacing the light source which then further entails having to accept other spectral differences, for example those induced by technical production contingencies.

Another disadvantage of such measuring devices employing conventional irradiation sources is their low measuring frequency and also the length of time which is required after switching on the device before one can render a usable measurement result, as conventional light bulbs require a relatively long period of time before they are able to emit a stable and reproducible spectral radiation. When attempting to ascertain a surface gloss measurement, should said surface be illuminated with a monochromatic light source such as a laser, for example, this results in the disadvantage that the gloss, respectively the reflection capacity, is then determinable solely for the illuminated wavelength.

The physiological impression an observer perceives upon illumination with daylight is created by evaluating as well as integrating that radiation to which the eye is sensitive; for each type of cone, an integration of the wavelength-dependent radiation is basically weighed against the wavelength-dependent sensitivity of the different cones through the wavelength. This means that with a monochromatic illumination, for example, different surfaces can render the same measurement results although the observer perceives the gloss of the surfaces differently and the reflection capacity differs at other wavelengths.

A monochromatic illumination thus has the disadvantage that nominally identical gloss, color or similar characteristics are determined from different surfaces although the physiologically perceptible parameters clearly differ.

BRIEF SUMMARY OF THE INVENTION

It is therefore the task of the present invention to provide a method and a device of the type as indicated above to enable a reproducible and quantifiable evaluation of surface quality in order to enable the making of reliable assessments.

Another aspect of the task of the present invention is to provide a device which is of more compact and simpler construction such that a user can easily take it with him and employ it to evaluate a surface without the need for utilizing any other aids.

A further aspect of the task of the present invention is to provide a device for measuring visual characteristics of a surface which, despite said device's compact construction in accordance with the previously stated aspects of the tasks of the invention, considerably improves upon measurement reproducibility as well as upon the intervals of time necessary between maintenance and recalibration in comparison to known prior art devices.

A device according to the present invention used for making quantified determinations of the quality of surfaces comprises an optical system having a first and a second optical means. The first optical means comprises at least one illuminating means which emits light directed at a predetermined angle onto a measurement surface which is part of the surface to be measured. The second optical means is likewise aligned at a predetermined angle to the measurement surface and receives the light reflected from said measurement surface. Said second optical means comprises at least one photo sensor and emits an electrical measurement signal characteristic of the reflected light.

The inventive device furthermore has a control and evaluation means, provided for controlling the measurement sequence and for evaluating the measurement results and which consists of at least one processor device and at least one memory means. An output means (display) serves to display the measurement results.

The illuminating means further comprises at least one light source, configured in the present inventive device as a light-emitting diode (LED). The radiated light is configured such that its spectral characteristic comprises preferably at least blue, green and red spectral components in the visible light spectrum.

Furthermore, a filter means is additionally disposed in the path of radiation between the light source and the photo sensor which changes the spectral characteristics of the incident light in accordance with predetermined filter properties so as to result in the spectral characteristic essentially approaching a predetermined spectral distribution.

The evaluation means assesses the light reflected by the measurement surface and derives at least one parameter therefrom which characterizes the measurement surface, respectively the surface itself.

The device according to the present invention has numerous advantages.

A decisive advantage of the invention is that the position of the light source as well as the light-emitting surface and the amount of emitted light is precisely defined with respect to the device. With conventional light or halogen bulbs and the like, the member which emits light is the filament, which is usually held in place in the glass body of the light bulb by means of thin wires. This type of spring-like suspension has the effect that even minor shaking or vibration can induce changes in the position of the light-emitting source, the filament respectively. Thus an exact determination or prognosis of the intensity and direction of the propagated radiation is only possible with considerable effort, if at all.

In contrast thereto, by employing an LED as the light source, the position of the light-emitting member, the light-emitting surface respectively, is defined precisely and does not vary over time, even due to factors contingent upon aging. This substantially improves the reproducibility and precision of the measurement of surface quality.

Also advantageous is that using an LED as light source when determining a parameter allows for an increased frequency of measurement, respectively a reduced cycle duration. The light sources in present known devices are usually turned off, only to be turned on at the time of measurement, in order to reduce internal scattered light within the device. While a typical light bulb requires at least 1 to 1.5 seconds to attain an essentially stable emission of radiation, the comparable timeframe for a light-emitting diode amounts to only about 0.1 to 0.2 seconds, sometimes even less. It follows that the measurement frequency can be increased by a factor of approximately 7 to 15. A measurement cycle when employing an LED typically takes less than 0.2 seconds, while approximately 1.5 to 2 seconds are required when utilizing a light bulb.

Another advantage of a device according to the present invention is that contingent upon the spectral characteristic of the light source, preferably exhibiting at least blue, green and red spectral components in the visible spectrum, the surface is illuminated with different wavelengths and the surface parameters to be measured can be reliably determined.

As the light-emitting source according to the present invention is subject to only minor age-contingent changes to the emitted spectrum, the daily calibration necessary with conventional devices is no longer necessary. With the device according to the present invention, it is sufficient to carry out an occasional calibration using a measurement standard, for example twice a year. Should measurements frequently be conducted under dusty or dirty conditions, it may be sensible to increase the frequency of calibration in order to curb the influences of dirt and dust which settle or deposit on the optic elements employed.

A reduced frequency of recalibration for a device in accordance with the present invention is extremely advantageous since, in addition to saving time, possible errors which might occur during the recalibration process are avoided. This includes operator errors as well as faulty calibration standards such as, for example, those which are contaminated or damaged.

Another advantage of the inventive device is that the filter means allows the spectral characteristic of the light employed for the measurement to closely approach a predetermined spectral distribution, which in turn enables measurements to be conducted pursuant to national or international measurement standards.

In a preferred embodiment of the present invention, the light source, the light-emitting diode of the illuminating device respectively, transmits light of a continuous spectrum whereby the spectral distribution of the transmitted radiation exhibits considerable spectral components of the blue through red spectral range. Preferably, the wavelength-dependent spectral intensity of the transmitted radiation in the wavelength range between 480 and 620 nm is greater than one-hundredth of the maximum spectral intensity; especially preferred is the relative wavelength-dependent intensity in the wavelength range between 440 and 680 nm being greater than one-hundredth of the maximum wavelength-dependent intensity; and most preferred is the emission of considerable intensity through essentially the entire visible spectral range.

Preferably, the light transmitted by the light-emitting diode of the illuminating device is structured in such a way that the color of the emitted light is essentially "white."

Such an embodiment of the inventive device is especially advantageous since light source intensity is emitted over a wide bandwidth, respectively the entire visible spectrum, so that essentially all the relevant wavelengths can be taken into consideration in determining the surface characteristics.

In a preferred embodiment of the present invention, the filter means is provided with an optical filter element arranged as a transmission filter in the light path between the light source and the photo sensor, whereby especially preferred is that the filter, the filter means respectively, is arranged on the first optical means.

In this embodiment, the spectral distribution of the light emitted by the light source is modified by at least one optical filter before it impinges on the surface to be measured, thus enabling an adjustment of the emitted spectral distribution to a predetermined spectral distribution.

Employing a transmission filter in the filter means is advantageous because it enables the utilization of a particularly simple, inexpensive and uncomplicated illumination process for the measurement, thus avoiding the need for costly and time-consuming harmonizing adjustments, which could become necessary by virtue of multiple redirecting (bending) of the light rays.

In another preferred embodiment of the present invention, at least one reflection filter, respectively a reflection filter element, is provided in the filter means which reflects the impinging light. The nature of this at least one reflection filter is such that it enables the spectral distribution of the reflected light to be influenced in such a way that it essentially adapts to a predetermined spectral distribution. Said reflection filter can be arranged in the first optical means, in the second optical means, or at another location within the device, whereby the filter is then preferably located at a spot where light ray redirection is necessitated.

In another preferred embodiment, the filter means comprises two or more optical filters, whereby some or all filters, respectively filter elements, may be disposed as transmission filters and some or all filters as reflection filters.

The optical filters employed in the (one or more) filter means are conventionally manufactured optical filters as already known in the prior art, hence, for example, configured as glass plates or glass wedges, preferably of quartz glass, which can exhibit an appropriate coloring. It is however also possible to make use of filters made from plastic material, crystals, interference filters, holographic transmission and reflection filters, liquid filters and the like. It is moreover possible that a filter is configured to be fluorescent so that it will absorb impinging radiation within a certain wavelength range and re-emit same as a ray having a different frequency, respectively wavelength. This enables not only the so-called "subtractive color mixture" but also the so-called "additive color mixture," thus allowing a spectral distribution not only through attenuation of certain spectral ranges but also through increasing of certain other specific spectral ranges.

Employing a filter means of this type is especially advantageous since—using simple design measures—it is possible to achieve an effective, specific and cost-effective control or variation of the spectral distribution. Using relatively thin filters as transmission filters is especially advantageous since same can be introduced directly into the light path while still allowing the device to remain compact. On the other hand, when using reflection or fluorescent filters, a redirection of the beam can be required as well as beneficial in order to provide an overall compact device.

In a preferred embodiment, the characteristic parameter of the measurement surface to be determined by said device is surface gloss. Determining of gloss is particularly advantageous because gloss is an especially significant characteristic optical parameter of a surface, one which has considerable effect on the quality of a surface.

In a preferred embodiment of the present invention, two, three, four, five or more characteristic parameters, preferably optical, are determined for the measurement surface.

In a preferred embodiment of the present invention, the characteristic parameter to be determined by said device is one from among a group of parameters which encompasses gloss, haze, distinctness of image (DOI), color and color brightness.

It is additionally possible that the characteristic optical parameter of a representative measurement for the typical wavelength and amplitude (orange peel) of the topology of the measurement surface is in a predetermined wavelength interval, whereby this evaluation may also be carried out in two or more wavelength bands.

In the preferred embodiment of the present invention in which two or more characteristic parameters of the measurement surface are determined, the individual parameters are selected in accordance with the above-cited parameters.

Determining a parameter for the haze or DOI is particularly advantageous because an observer's physiological impression of, for example, a finished surface is decisively dependent upon its DOI and its haze. The determination of a parameter for color is also highly advantageous, for example to ensure that when refinishing or touching up a damaged area (of the surface), the necessitated reliable and reproducible determination of color is achieved, so as to enable a quantitative comparison of the refinished area with the total surface. Determining of color, respectively deriving a color parameter, is also important to enable regular quality control during ongoing series production.

Determining of an orange peel parameter is particularly advantageous in, but not limited exclusively thereto, production processes when manufacturing finished surfaces because the wavelength distribution of the surface structure can reveal information about deficiencies in the production process which can then be minimized or eliminated.

In a preferred embodiment of the present invention, the predetermined spectral distribution is a standard distribution corresponding to one of the common light standards, and preferably one which emits a light type taken from among one of the groups encompassed by the C, D65, A or similar light type standards as, for example, defined by the Commission Internationale de l' Éclairage.

Using such a standard distribution as the predetermined spectral distribution is especially advantageous in that the determination of the measurement results is conducted employing a known, respectively normalized, spectral distribution or light type, thus ensuring a high degree of comparability with other measurement results. Furthermore, carrying out the measurements using such a standard spectral distribution or its equivalent has the particular advantage that measurement results are obtained which can be reproduced under typical conditions. Illumination and measurement using the light type D65 or especially C standard ensures a measurement which corresponds to international standards.

The adaptation of the spectrum preferably transpires such that the measurement spectrum employed corresponds wholly to a spectrum as received by the average observer. This means that the entire device comprises a spectrum equivalently corresponding to "daylight," respectively light type C or similar, adjusted to the sensitivity of the light-acclimated eye $V_{(\lambda)}$. This is to be understood as to mean that the aggregate of the spectra of the light source, the filter employed, the other optical elements and means as well as the photo sensor correspond to the cited aggregate of daylight spectrum and eye sensitivity.

In a preferred embodiment of the present invention, the first optical means has an aperture which transmits a defined angular portion of the light emitted from the light source. Preferably said first optical means also comprises a lens arrangement which essentially parallelizes the light emitted from the light source.

Additionally, the first optical means may be provided with a scattering means, preferably in the form of a least one scatter disk which can then be arranged in the aperture opening for example, in order to achieve a homogenous light distribution across the aperture/scatter disk surface and thus guarantee a homogenous and uniform illumination of the surface to be examined.

The scatter disk arrangement comprises preferably at least one scatter disk which is configured as a plane-parallel or wedge-shaped plate. When operating the device according to the present invention with only one light diode as the light source, the scatter disk, respectively scatter disk arrangement, can be configured to be relatively thin or with only minor scatter effect since only the light from one light source must be homogenized through the aperture, respectively aperture of the scatter disk.

With known devices which use multiple light sources, it is necessary to use scatter disks of greater scatter intensity having no or very little color variation in order to achieve sufficient homogeneity of the radiation distribution. A disadvantage of this is that a higher percentage of the intensity is scattered and thus not available for the measurement task.

The light being scattered in other directions and the lower intensity of the measurement beam leads to a poor signal-to-noise ratio and thus less accurate measurements.

Using the device according to the present invention results in attaining higher illuminating intensity and simultaneously the generating of a reduced light noise component, the consequence being a better signal-to-noise ratio and qualitatively better measurement results.

In another preferred embodiment of the present invention, the second optical means is also disposed with a lens and aperture arrangement, whereby the lens arrangement essentially focuses the light reflected from the surface and the aperture stops down scattered light so that highly qualitative, reproducible measurement results are achieved.

In a further preferred embodiment of the present invention, the illuminating means has at least two or more light sources, preferably light diodes, whereby the individual light diodes may either have the same spectral characteristics to increase the illumination intensity or differing spectral characteristics in order to increase a specific spectral component.

This should be understood as to mean that in addition to one light diode which emits radiation over a wide spectral band, an additional one or more light or laser diodes or the like are disposed in order to amplify a specific spectral band.

Such an arrangement is particularly advantageous in that it allows the emitted spectrum to exhibit an even closer proximity to a predetermined spectral distribution, for example that of the C light standard.

In a preferred embodiment of the present invention, the control and evaluation means analyzes the measurement signal using a program stored in the memory, and preferably saves the measurement signal and/or the analyzed measurement results and/or the parameters as derived in said memory.

This has the advantage that the measured signals or the parameters are available even after the measurement process has been completed.

In a preferred embodiment of the present invention, the second optical means comprises a number of photo sensors, preferably arranged adjacent to each other, whereby the individual photo sensors can be arranged in a row or over a surface section, for example in rows and columns. In this way it is possible to incorporate a number of photo sensors, although not all of them are required to be used for every measurement, respectively not all the measurement signals from all the photo sensors will need to be evaluated.

Additionally it is possible to switch between a number of said photo sensors, respectively their measurement signals, in such a way that a common measurement signal can be determined from said variable photo sensors which is then representative of the incident light.

In this way, individual sections of all the photo-sensitive surface areas of all the photo sensors can be switched to variably form one or more measurement areas, realizing programmed measurements in accordance with international measurement standards. In a further preferred embodiment of the present invention, at least a first part of the light radiated from said first optical means exhibits a light pattern, whereby said light pattern preferably comprises at least one light/dark edge. The transition from light to dark is preferably very distinct. Through the evaluation of such a light pattern it is possible to determine, for example, surface orange peel.

It is additionally possible, for example, to determine the structural definition of structured surfaces. The light pattern is preferably generated using a transmission pattern device and may also be varied. Besides for conventional grids or line grids which exhibit blackened or grayed regions and transitions therebetween, variable pattern generators such as liquid crystal, LCD (liquid crystal displays) or electro-optical crystals or switches, e.g. Pockel cells, may be employed.

In a preferred embodiment of the latter described embodiment, a plurality of light/dark edges are provided of which at least one part thereof extends at least sectionally parallel to one another. Preferably at least one section of said plurality of light/dark edges is of a form taken from a group of forms encompassing grid, cross-mesh, ellipse, circular and the like.

When employing a variable pattern means, e.g. an LCD device, different patterns can be switched between and projected, thus enabling versatile and variable usage.

The arrangement of a plurality of light/dark edges which extends at least sectionally parallel or symmetrical to one another is particularly advantageous because when using multiple photo sensors, the progression of the individual light/dark edges, respectively the determination of this progression on the photo sensors, enables information to be obtained about various surface properties of the measured surface.

In a preferred embodiment of the present invention, the evaluation means derives at least one gradient of the measurement signal from the difference between the measurement signal of one photo sensor and the measurement signal of at least the next photo sensor. Thus at least one gradient in the measurement signal is preferably determined for at least some of the photo sensors.

Preferably, the evaluation means in the present preferred embodiment is so configured that at least an average parameter for at least a portion of the gradient can be determined and that, as a result, a characteristic variable can be determined for the surface, whereby preferably, and in particular for structured surfaces, a characteristic structural variable can be derived.

Determining the gradient and the mean gradient is particularly advantageous because this can reveal information about the orange peel and roughness of the surface to be measured. A smooth or flat surface depicts projected light or dark lines, respectively light/dark edges, on the one or more photo sensors which are of sharp distinction so that a high maximum gradient is ascertainable. Rough or rippled surfaces depict a less distinct light pattern, so that the individual gradient value, the maximum gradient and the mean gradient can be less. In contrast, structured surfaces, for example those with saw-tooth-like or triangular surface profiles, ideally depict a distinct light pattern, whereby however the path of the individual edges, respectively the light pattern, can show skips, offsetting or similar distortions.

In a preferred embodiment of all previously-described embodiments of the present invention, a third optical means with at least one light source is provided. The light source radiates light at a predetermined spectral characteristic which is directed at a predetermined angle onto the surface to be measured. The light from said third optical means is preferably directed onto the surface to be measured at such an angle that the light directly reflected from the measurement surface in accordance with the Fresnel reflection has a different angle relative the surface as the angle between said measurement surface and the light reflected from said measurement surface as emitted from the first optical means.

Such an arrangement has the advantage that the directional reflection of the light emitted from the third optical means does not overlap the directional reflection of the light emitted from the first optical means.

In a preferred embodiment of the embodiment of the present invention comprising a third optical means, the spectral characteristic of the light emitted from said third optical means is such configured that a determination of surface color, respectively a color parameter, is possible by evaluating the light reflected from said surface. For this purpose, said third optical means may be disposed with one or more light sources, whereby the spectral characteristics of the individual light sources may be the same, for example in order to increase the intensity.

It however may also be the case that the individual light sources of said third optical means have different spectral characteristics, in case the light sources used do not cover the visible spectrum to a substantial degree.

A light diode exhibiting emitted light which is essentially "white" is particularly preferable as the light source of the third optical means. Using such a light source enables a determination of surface color. The light source employed in said third optical means should comprise at least the red and green, and preferably also blue, spectral components in its emitted spectrum.

In a preferred embodiment of one or more of the previously-described embodiments of the present invention, at least one photo sensor has at least two, preferably three or more, photo-sensitive elements, the electrical output signals of which can be ascertained individually and which differ in their spectral characteristics, respectively sensitivity.

It is possible, especially when the photo sensor(s) employed each have three photo-sensitive elements, to determine the color of the measurement surface as an optical parameter. Preferably, a plurality of photo sensors each have three photo-sensitive elements, their spectral characteristics are configured in such a way that the color of the incident light can be ascertained.

In this case, it is preferable to employ a color CCD chip—for example a color CCD chip as used in commonly-available video or digital cameras and having a pixel count in the five or six digit range. CCD chips (color) having highest qualitative properties can also be employed.

The determination of color, a color parameter respectively, of examined surfaces is very advantageous because color tone is an important property of many technical products. Especially when refinishing damaged areas, but not limited exclusively thereto, the refinished part of the surface should have the same color tone as the rest of the item in question, but additionally, for example in series production, it is important that all items from one or several different series have the same color.

In a preferred embodiment, at least one, preferably at least the first optical means, emits essentially parallel light. It is, however, also possible that at least one, preferably at least the third optical means, emits essentially divergent or convergent light.

In a preferred embodiment of the present invention, the predetermined angle at which the light emitted from at least one of said optical means is directed onto the surface is an angle selected from among a group of angles which include, in particular, the angles of 0°, 5°, 10°, 15°, 20°, 30°, 45°, 60°, 75°, 80° and 85°, whereby these angles are defined as the angle between the rays (incident or emergent) and the vertical, respectively normal, to the measurement surface. It is especially preferable that the angles at which the first and second optical means are aligned to the surface are identical.

The alignment of the optical means in accordance with the angles as described above is particularly advantageous since it enables measurements to be conducted which correspond to the various national and international standards (the American ASTM E430 standard, the ISO 2813, the DIN 67530 and equivalents).

In a preferred embodiment of the present invention, a second and preferably also a third optical system is provided, whereby the arrangement of an optical system relative the surface to be measured is preferably at 20°, 60° or 85°. In the event that three optical systems are provided, then preferably one will be aligned at 20°, a second at 60° and a third at 85° relative to the normal to the surface to be measured.

It is also possible that a further optical system, respectively optical means, is provided for a separate color measurement and which would then be aligned, for example, at 45° to the normal to the surface.

The above-cited angles of 20°, 60° and 85° relative to the normal to the measurement surface are especially, but not exclusively, applied when determining the gloss of the surface being measured. The 20°-geometry is specifically suited for high gloss reference blocks, while the 60°-geometry is essentially suitable for all surfaces. The 85°-geometry is preferably selected in order to achieve a better differentiation in surfaces in which the gloss at the 60'-geometry is less than 10 units according to the ISO 2813. It is preferable to calibrate the optical means for the 20°, 60° and 85° alignments with an accuracy greater than ±0.1°.

In a preferred embodiment of one or more of the previously-described embodiments, at least one optical means, preferably at least the first one, radiates at least one light strip having a predetermined length and width perpendicular to the direction of propagation at a predetermined distance from the light source.

In a further preferred embodiment of the present invention, at least one temperature measuring means is disposed as close as possible to at least one light source and/or at least one photo sensor, provided for determining the characteristic temperature of each respective light source or photo sensor, in order to enable a temperature-corrected determination of at least one parameter.

It is also possible that the temperature determination of the individual components (light source, photo sensor or photo-sensitive element) transpires directly at the component itself and, in particular with light diodes and photocells, it can be possible to ascertain the temperature determination by measuring the no-load voltage or the short-circuit current or equivalent values. Determining temperature in this manner yields especially high reliability because due to dynamic processes, no or extremely low heat capacity can corrupt the temperature determination.

Determining the temperature of the individual members is particularly advantageous since the temperature of the individual members (light source, sensor) changes the spectral properties. Determining the temperature allows a more accurate measurement.

In a preferred embodiment of the present invention in which a light pattern is emitted, preferably at least a portion of the progression of the at least one light/dark edge depiction is defined on the plurality of photo sensors. After determination of the progression, a deviation of the measured path from the ideal path is derived and a characteristic surface parameter of the measured surface determined.

This surface parameter can characterize, for example, the height of a profiled surface, but this parameter can also be determined in such a way that it indicates the steepness to the profiled surface or the distinctiveness of the edges of the profiled surface.

Determining such a surface parameter is of particular advantage when measuring structured surfaces, such as those which are present in, for example, automobile interiors.

In a preferred embodiment of all previously-described embodiments, the device is moveable relative to the measurement surface at an essentially constant spacing therefrom and a distance measuring means is provided which quantitatively tracks this relative movement.

A memory is also preferably provided into which the parameters and/or the optical parameters measured along the predetermined measurement points on the surface are stored.

A measurement wheel is also preferably provided, which is positioned upon the surface to be measured during the measurement and which rotates during the relative movement between the device and the surface being measured, whereby then preferably at least the measurement wheel is coupled with a rotating angle output device which emits an electrical rotating angle signal representative of the rotation angle returned by the measurement wheel.

In a preferred embodiment of one, several or all of the previously-described embodiments, a comparison means is provided in the device and at least one but preferably a plurality of two, three, four, six or more reference parameters, respectively reference parameter pairs, are stored within a part of the memory, said reference parameters having been determined from the measurement of specific, preferably differing, reference surfaces or reference standards and having been preferably determined by said device.

In addition to these reference values, respectively reference parameters, preferably also the electrical measurement signal of at least one photo sensor is concurrently returned, so that preferably a table is created in the memory which contains at least one photo sensor electrical output signal for predetermined measurement standards, respectively reference surfaces.

When conducting a measurement, it is preferable to compare the electrical output signal, respectively measurement signal of the photo sensor with the values in the table which correspond to the reference surfaces. After selecting the two nearest values, the electrical output signal of the photo sensor is set with reference to these two stored values. An interpolation, preferably linear, is then made between the value(s) stored in the table and a parameter for the surface to be measured derived. The evaluation with said comparison means can be used for determining gloss as well as all other parameters.

Such a configuration is highly advantageous since, particularly when determining reference pair values with said device, the system-contingent losses and properties are concurrently ascertained as well. Additionally, it is possible to take into account non-linearities in the entire device, respectively in the sensors. Thus, the accuracy of the measurements can be increased considerably because, particularly with relatively high light intensities, the linear range of the sensors is transcended and saturation occurs.

The prerequisite for a linear relationship between intensity and sensor signal is then only fulfilled in a small range and no longer throughout the range from "zero" to the measured value. An interpolation between adjacent values is however also possible in this instance and furnishes a good reading.

BRIEF DESCRIPTION OF THE DRAWING

Further advantages, features and application possibilities of the present invention will now be specified in the following description of embodiments in association with the drawings, which show.

DESCRIPTION OF THE INVENTION

A first embodiment of the present invention will now be described with reference to FIGS. 1-5.

Figure 1:
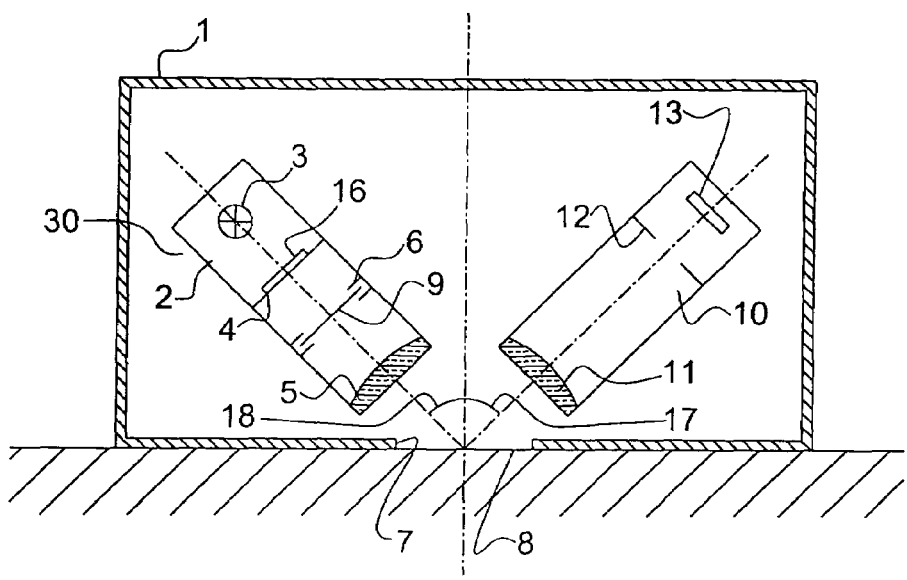
FIG. 1 a sectional view of a device in accordance with a first embodiment of the present invention.

The measuring device for determining the quality of surfaces represented sectionally in FIG. 1 has a housing 1 with an opening 7 provided therein. The device is placed with opening 7 on measurement surface 8. A first optical system 30 is arranged within the device which comprises a first optical means 2 and a second optical means 10.

The optical axes of both optical means 2, 10 are arranged at angles 17, 18 to the vertical of measurement surface 8. In this embodiment, angles 17, 18 have been selected to be symmetrical and amount to 45°. As a variation of the device, and especially for gloss measurements, an angle of 60° is preferred.

In first optical means 2, a light source 3 is disposed which is configured as a light diode and its emitted spectrum essentially exhibits intensity throughout the entire visible range.

The light radiated from light diode 3 impinges upon scatter disk 16, which in this embodiment is arranged in front of an aperture 4. Scatter disk 16 can be a surface or volume scatter disk which evenly distributes the light radiated from light diode 3 over the entire opening of aperture 4, so that the light passing through aperture 4 and especially over the surface to be measured has a homogeneous intensity distribution.

A filter means is disposed in the subsequent path of radiation comprising a filter retainer 6 in which a spectral filter 9 is arranged. In this embodiment, filter 9 of the filter means is arranged as a transmission filter and consists of suitably-colored quartz glass and has the function in this embodiment of modifying the radiated spectrum from light source 3 so as to substantially approach the radiated spectral intensity as that of the C light type standard.

The filter means modifies the spectrum in such a way that a measurement spectrum is employed which is proportional to the aggregate of the spectra from eye sensitivity of the light-acclimated eye $V_{(\lambda)}$ and the spectrum of C light type standard.

Lens 5 in first optical means 2 parallelizes the emitted light, which then impinges upon measurement surface 8 and there, in accordance with the Fresnel Law of Reflection, is reflected at the same angle as that at which it impinged.

The light reflected from the surface, measurement surface respectively, enters the second optical means 10 and is focused by lens 11 as therein disposed. Additionally an aperture 12 is disposed in second optical means 10, which essentially transmits solely the relevant rays and components, so that photo sensor 13 arranged downstream thereto receives only the light reflected from the surface. Aperture 12 has the function of a Fourier filter in said second optical means 10.

The light radiated from diode 3 exhibits a spectrum 21, which radiates intensity in the represented region between 380 and 770 nm, with a first, absolute maximum radiation of between 460 and 490 nm at about 475 nm and a further relative maximum between 560 and 580 nm.

The intensity is plotted in relative units in relation to the maximum radiated spectral intensity. Apart from curved plot 21, individual measurement points or reference values 21a are plotted, which are depicted as blackened squares.

The light diode employed, for instance a light diode from the Nichia company, has spectral components in a region between about 430 and 740 nm, which are greater than 2% of the maximum spectral intensity.

Figure 3:
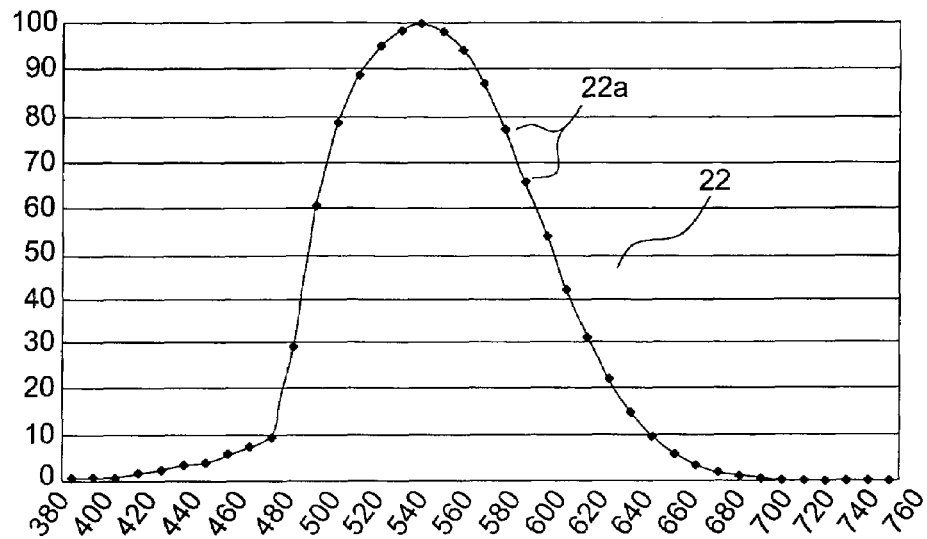
FIG. 3 the filter spectral transmission in the embodiment according to FIG. 1.

The spectral path 22 of transmission filter 9 of first optical means 2 shown in FIG. 3 has a maximum transmission at about 550 nm; the transmission rate of filter 9 reduces at shorter wavelengths. Measurement points 22a of spectral transmission 22 are likewise plotted in FIG. 3 at an interval of about 10 nm.

The transmission rates plotted through the wavelengths are likewise standardized; i.e., plotted with reference to the maximum transmission, so that same reaches approximately 100% in said specified area.

Figure 4:
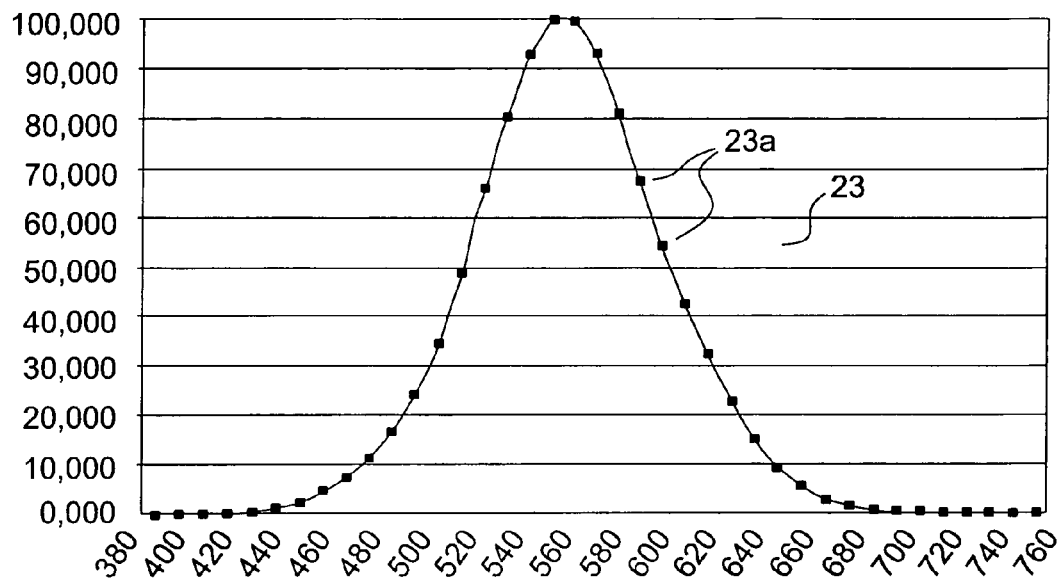
FIG. 4 the spectral sensitivity of the light-acclimated human eye with illumination in accordance with the C light type standard.

FIG. 4 depicts the spectral intensity 23 through the wavelengths of an ideal measuring system, whereby individual measurements points 23a are likewise plotted at an interval of approximately 10 nm. As in FIGS. 2 and 3, a relative intensity is plotted, referenced to the maximum spectral intensity, and thus encompasses values between 0 and 100%.

For measurements complying with the international ISO 2813 standard, $3^{rd}$ edition from Aug. 1, 1994, it is mandatory to use the CIE (Commission Internationale de l' Éclairage) C light type standard for measuring surface gloss. Respectively, for measurements of surface gloss, a spectral function of the device must have such properties as are necessary to ensure a spectral measuring process, which in turn results in an illumination in accordance with C light type, adjusted for the spectral eye sensitivity of the light-acclimated eye $V_{(\lambda)}$.

Filter 9 is interchangeable and can be replaced by a filter which generates a measurement spectrum for the darkness-acclimated eye $V'_{(\lambda)}$ (c.f. e.g. Bergmann Schaefer, *Lehrbuch der Expermentalphysik*, Vol. III, Optic, $8^{th}$ edition, 1987, pages 674 et seq., 718, 730-743).

Such a spectral distribution has the advantage that, for example, gloss is determined with a spectral distribution which corresponds to daylight illumination, whereby the eye sensitivity of the "average" or "standard" person is taken into account.

In such a device, gloss measuring apparatus respectively, the spectrum is influenced by various components. The light radiated from the light source is spectrally influenced in various different ways by the various optical components such as lenses, filters and other similar components.

The spectrum is influenced not only by the surface to be measured but also by the spectral sensitivity of the sensors employed, so that the measured result yields from the aggregate of the spectral processes from light sources, scatter disk arrangements, optical filters, other optical elements used such as lenses or similar items, as well as the sensors multiplied by the spectral reflection capability of the surface being examined.

Figure 2:
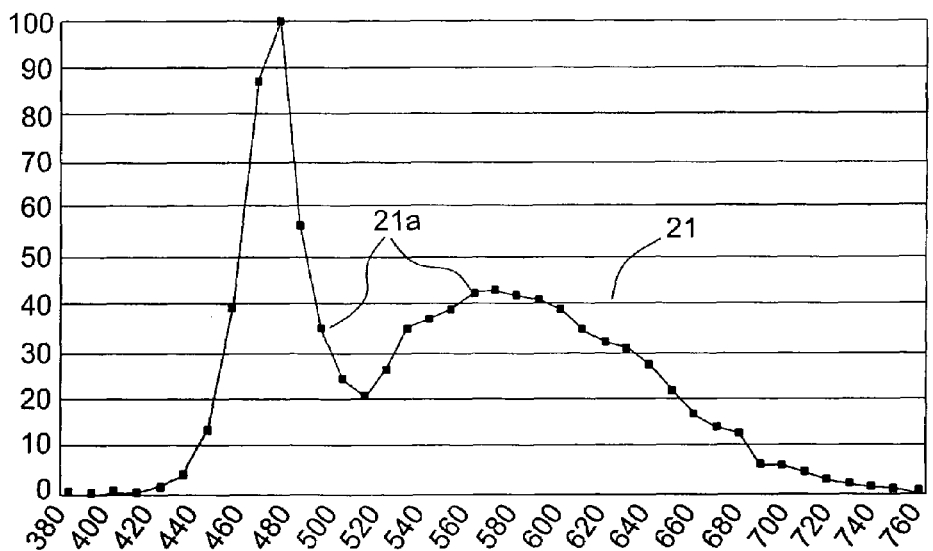
FIG. 2 the light source wavelength intensity distribution in the embodiment according to FIG. 1.

The first-mentioned influences define the device spectrum, which should approach the spectrum as shown in FIG. 2, 3 in order to enable the taking of measurements in compliance with the ISO 2813.

With the gloss measuring device according to the present invention, the spectrum approaches the ideal spectrum in that a light diode is employed with a spectrum 21, as represented in FIG. 2, in conjunction with a filter means having a spectral path 22, as represented in FIG. 3.

Figure 5:
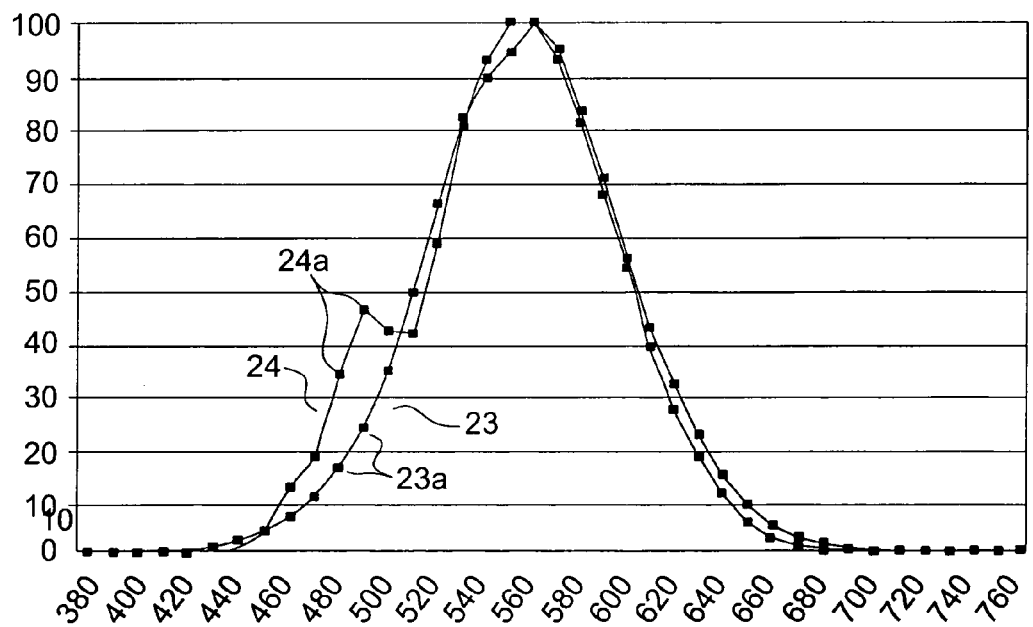
FIG. 5 a comparison of the set-actual spectra with the device in accordance with the embodiment according to FIG. 1.

The complete device properties together yield a spectral path 24, represented in FIG. 5. In comparison, the ideal spectrum 23 is plotted in FIG. 5 whereby individual measurement points 23a and 24a of the actual and the ideal spectra are additionally indicated. In the region shown, the variations between the actual and the ideal spectra are small, so that a good correlation with the measurement conditions prescribed in ISO 2812 may be assumed.

In particular, both spectra exhibit the absolute maximum at about 570 nm; the sides are also virtually congruent at about 50% of the maximum intensity. In the red range of the spectrum between 600 and 700 nm, the ideal and the actual spectral paths correspond to a very precise degree.

In the present embodiment, the photo sensor is a CCD chip in which the electrical output signals of the individual photo elements can each be determined individually. Different pixels in the CCD chip can be linked to individual sensors so that further differing sensors of differing dimensions are effectively geometrically arranged at different positions.

Parallel light, when reflected from an ideal mirror, impinges the second optical means as parallel light, it is focused there by lens 11 as arranged there, and then impinges photo sensor 13 of the second optical means; its signal enlisted in deriving the gloss.

With a non-ideally reflecting surface, a portion will be reflected diffusely so that other parts of the CCD chip are additionally illuminated. These portions of the received light can be used to determine haze, DOI and orange peel.

The division of the CCD surface into different sensors is controlled via control means (not shown) and can transpire in such a way that optical parameters can be measured in accordance with different international and national standards such as, for example, the American ASTM E 430 standard.

A second embodiment will now be described with reference to FIGS. 6 and 7.

Figure 6:
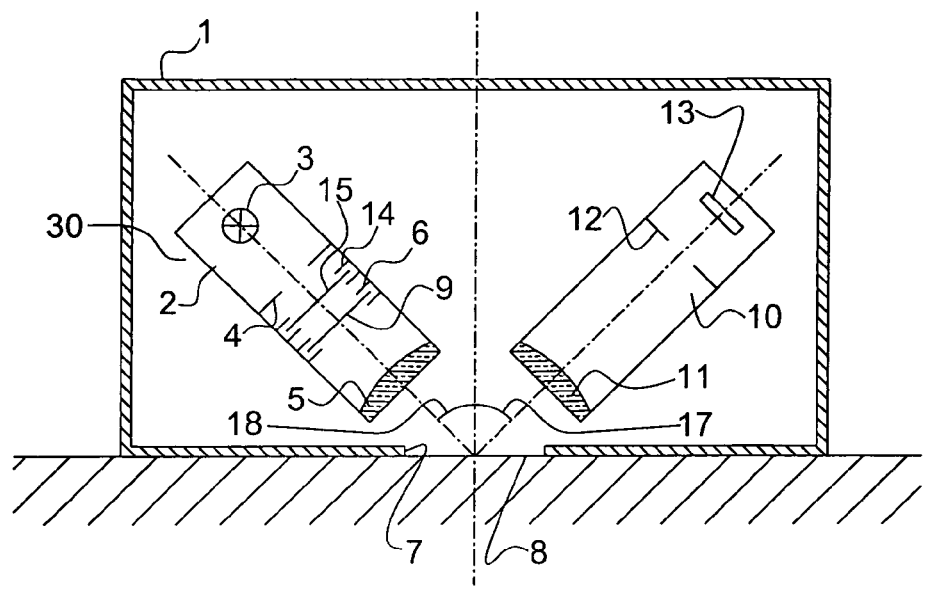
FIG. 6 a second embodiment of the device in accordance with the present invention in which a light pattern is projected onto the surface to be measured.

As far as it is feasible with respect to the optical measuring device represented sectionally in FIG. 6, the same reference numerals are used as those in the measuring device represented in FIG. 1 and in all the other embodiments so that an explicit explanation of identical components can be omitted here.

Measuring device 1 has a housing 1 with an optical system 30 which comprises a first optical means 2 and a second optical means 10. In the first optical means 2, a light diode is arranged as light source 3. The light radiated from light diode 3 impinges upon a light pattern arrangement 15 held in retainer 14, which in this embodiment is configured as an amplitude grid. Depending upon the pattern, parts of the impinging light are absorbed while other parts are transmitted.

Figure 7:
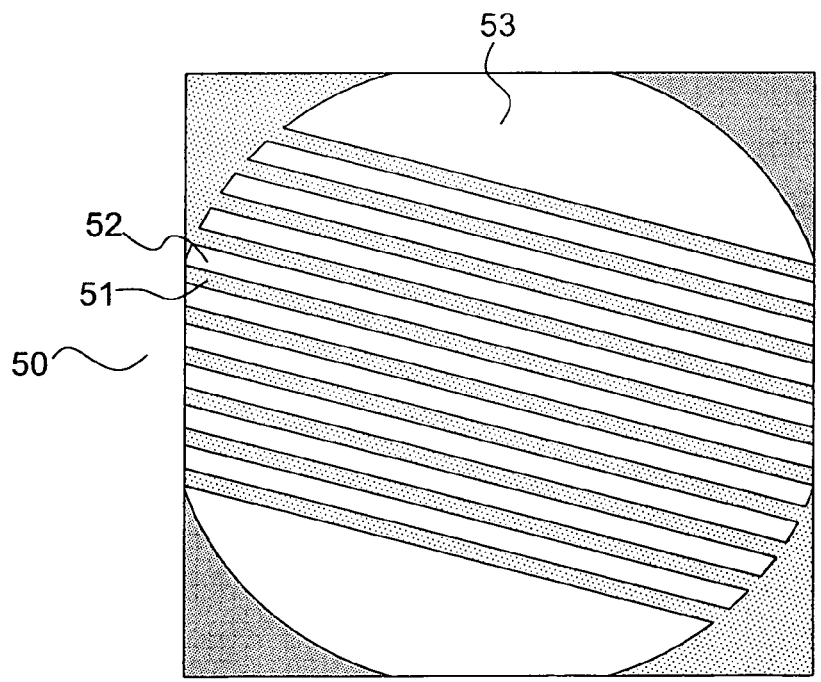
FIG. 7 the light pattern projected from the first optical means in accordance with the embodiment according to FIG. 6.

The projected light pattern 50 from first optical means 2 is shown in FIG. 7, comprising dark stripes 51 and light stripes 52 arranged as parallel stripes over the entire pattern section. Additionally, a part of the measurement surface comprising section 53 is illuminated which does not exhibit any pattern, so that, for example, the gloss can be determined by evaluating the reflected light from measurement surface section 53 in the same way as in embodiment 1.

Downstream the light pattern plate, respectively light pattern arrangement 15, the light radiated from light diode 3 passes through optical filter 9, where the emitted spectrum 21 is adjusted to the ideal spectrum 23, so that in turn spectrum 24, as depicted in FIG. 5, is employed for the measurement.

This embodiment yields additional measurement possibilities for determining the optical parameters of a surface to be measured in addition to those described in accordance with the first embodiment.

With increasing roughness of a surface to be measured, the contrast of the light pattern falling upon the photo sensor reduces, so that an evaluation of the contrast between the light areas, respectively edges 52, and the dark edges 51 yields a value for the roughness of the measurement surface.

A poor gloss results in a lower intensity, whereby the contrast between light and dark areas does not have to change. Surface orange peel also results in a distortion of the individual dark and light lines, so that by evaluating the progression of these individual lines, conclusions can be drawn about surface orange peel or surface contortion.

Additionally, by evaluating the light pattern when measuring structured surfaces, conclusions can be drawn about the surface structure itself.

A rectangular profile will, if the light pattern is appropriately oriented, lead to offsetting of individual lines in the recesses, while a sawtooth or triangular profile on the surface to be measured gives rise to a corresponding line canting.

Various surface parameters can be derived by using, for example, digital image conversion in the control means (not shown).

In this embodiment, the intensity and the contrast of the recorded image are evaluated. Further, the gradient from one pixel to the next within the light pattern area is determined. Using weighted integration, respectively by establishing a mean value of the gradient or all gradients within the light pattern area, a characteristic parameter for the structure of the measurement surface can be determined.

Figure 8:
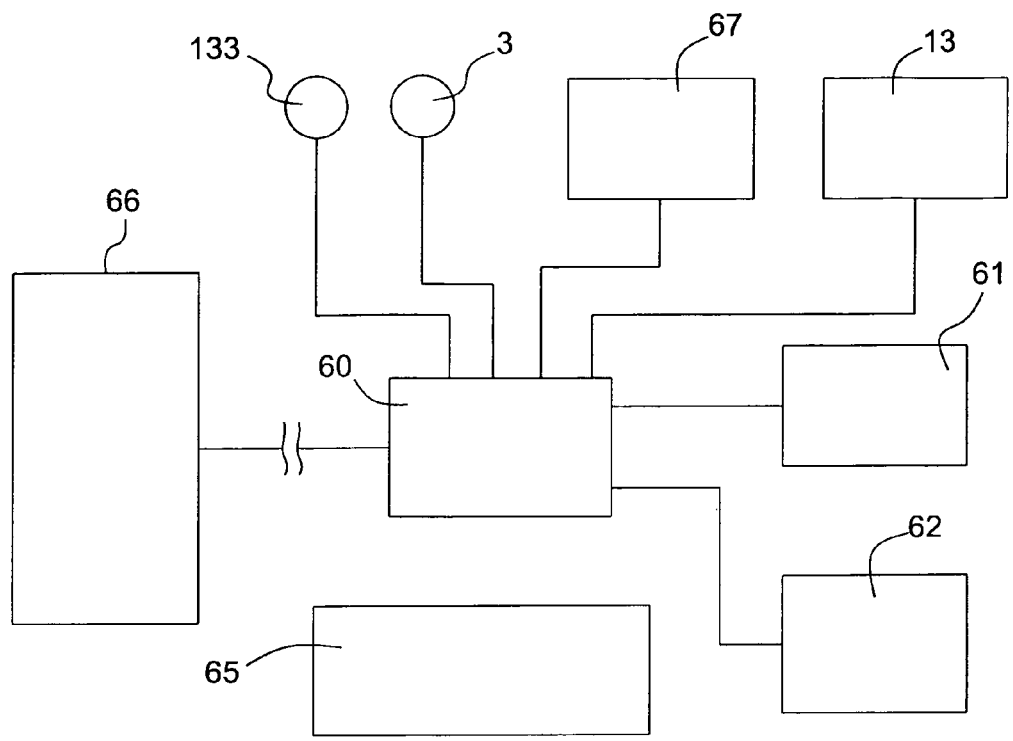
FIG. 8 the basic circuitry configuration of a further embodiment.

A third embodiment will now be described with reference to FIGS. 8 and 9 whereby in FIG. 8, the basic circuitry configuration is described, as is essentially also used in the embodiments according to FIG. 1 and FIG. 6.

The surface measuring device for the determination of gloss and other optical parameters has a light diode 3 as its light-emitting source, whereby the operation of the light source is controlled via control means 60, which contains a conventional commercial microprocessor.

Control means 60 is controlled by a program stored in memory 61. An input means 62 has a number of switches, various switching possibilities respectively, and has the function of inputting the control commands in order, for example, to start the measurement process or to select the optical parameters to be determined.

A display 65 is disposed as an LCD display and serves to display the measurement results.

Control means (60) is in electrical communication with at least one temperature measuring means (67). Temperature measuring means (67) is arranged as close as possible to the light source (3, 133) and/or the photo sensor (13). Control means (60) determines the characteristic temperature of each respective light source (3, 133)] or respective photo sensor (13) for the purpose of enabling a temperature-corrected determination of at least one parameter.

The device can be connected to an external computer 66 in order to be able to transfer the measurement results stored in memory 61 and conduct a more comprehensive analysis, archive the results or perform other similar operations.

Figure 9:
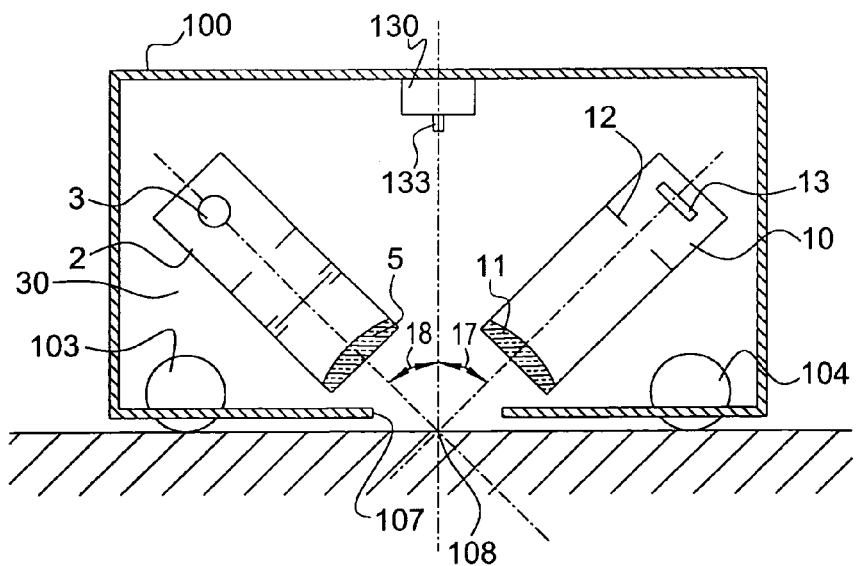
FIG. 9 a sectional view of a device in accordance with the embodiment according to FIG. 8.

The measuring device depicted in FIG. 9 has a housing 100 comprising the measuring optics and an opening 107. As in the previous embodiments, a first optical system encompasses a first optical means 2 and a second optical means 10, their optical axes each being aligned at angles 17, 18, respectively, to the normal to the measurement surface 108.

According to desired application, angles 17, 18 are preferably set at 20°, 45°, 60°, 85° or to another value, for example as defined in international standards.

In the first optical means, a light diode 3 is disposed as the light source, possessing the spectral properties depicted in FIG. 2 and thus radiating "white" light.

The light radiated from the first optical means, reflected from measurement surface 108 and received by the second optical means 10, is directed to the photo sensor 13 (disposed as a color CCD chip) in order to ascertain the color of the light received. The entire measuring device has an optical characteristic as represented in FIG. 5.

Additionally to the previous embodiments, a third optical means 130 is provided in the present embodiment which has a light diode as light source 133, its light being directed approximately perpendicularly onto the surface to be examined.

The light reflected diffusely from the surface at least partially impinges the second optical means and is received by photo sensor 13. Because optical sensor 13 is a color CCD chip having three adjacent spectral elements of differing photosensitivity, the color of the reflected light and thus the measurement surface can be determined.

A further difference from the embodiments described previously is that the device is not placed directly onto measurement surface 108 but rather is positioned by means of at least two rubber rollers 103, 104 or at least four rubber wheels 103, 104 (indicated schematically).

Rollers or wheels 103, 104 are rotatable (not represented) and arranged, respectively mounted, in housing 100. At least one wheel or roller is provided with a distance measuring means 67 (see FIG. 8) which records the angular movements of rubber wheels 103 and outputs an electrical signal representative thereof.

In this embodiment, the path covered by the device, respectively measuring means, is ascertained. The optical parameter (s) to be ascertained can be recorded at predetermined intervals along the measurement surface and then stored in memory 61 together with the location at which the measurement was made, so that even larger components or, for example, automobile bodies can be measured over a wide expanse.

Figure 10:
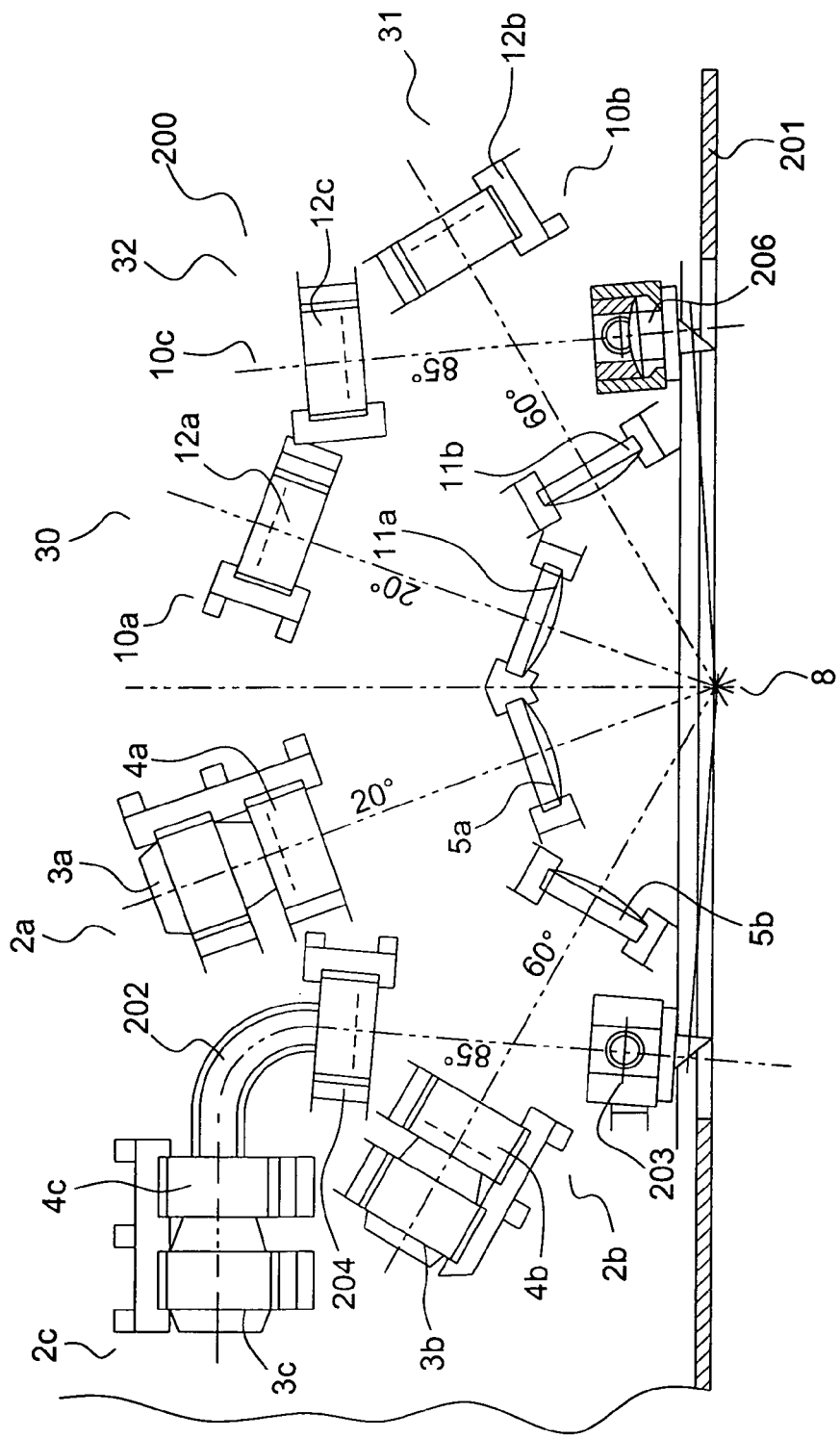
FIG. 10 a further embodiment of the present invention which has multiple sets of optical means.

FIG. 10 represents a fourth embodiment of a surface measuring device in accordance with the present invention in which three optical systems 30, 31 and 32 are employed. Each optical system comprises a first (2a, 2b, 2c) and a second optical means (10a, 10b, 10c.)

First optical means 2a and a second optical means 10a of first optical system 30 are each set at an angle of 20° to the normal to the measurement surface 8 in order to be able to reliably and accurately determine the optical parameters and in particular gloss of the surface to be measured should, for example, a high-gloss surface be assessed.

First optical means 2a contains a light diode 3a and a filter and aperture element 4a which modifies and adapts the spectrum emitted from the light diode in accordance with the spectrum as represented in FIGS. 2-5.

A lens 5a is also arranged in the path of illumination to the surface to be measured and a symmetrically arranged lens 11a focuses the light reflected from the surface onto the second optical means in which means 12a, comprising an aperture and a photocell, is arranged.

The second optical system 21 is connected in a similar manner to the first optical system, however, the likewise symmetrically arranged first optical means 2b and second optical means 10b are directed at an angle of 60° to the normal to the measurement surface 8.

This measurement geometry allows for ascertaining the gloss of essentially all surfaces to be measured. The measurement angle of 60° can be used to measure both poorly reflecting as well as highly reflective surfaces.

In accordance with the present embodiment, the inventive surface measuring device includes a third optical system, its radiated light is directed at angle of 85° to the normal to the surface to be measured.

First optical means 2c of third optical system 32 has a light diode as light source 3c and an aperture and filter arrangement 4c, so that the spectrum indicated in FIG. 5 with reference numeral 24 is employed as the measurement spectrum for the measurement.

The light radiated through the aperture and filter arrangement 4c of first optical means 3c of third optical system 32 is conducted via fiber 202 to aperture 204 and emitted more or less perpendicular to the surface to be measured. A prism 203 arranged near the surface redirects the light in such a manner that it impinges upon the measurement surface at an angle of 85° to the normal to the surface.

The reflected light is received by a prism 206 which then redirects the light toward photo sensor 12c in the second optical means of third optical system 32.

The 85°-geometry is especially suited for low-gloss surfaces.

The three optical systems 30-32 of measuring device 200 in accordance with the present embodiment are arranged in such a way that the light radiated from each of the first optical means in the differing optical systems intersects at a measurement point 8 on the surface to be tested, so that all three optical systems essentially illuminate the same measurement point, for which purpose a corresponding opening is provided in base plate 201 of the measuring device.

In all of the embodiments as described, the measured values are compared with the comparison reference values stored in memory 61, which were derived by measuring various reference standards, respectively reference surfaces. In this way it is possible to determine the optical parameters by an interpolation between contiguous parameters.

Furthermore, housing 1, 100 or 200 in all of the embodiments described is of compact construction, having the approximate size of a book, so that the user can simply carry the device with him and also use it for measurements of surface locations which are only accessible with difficulty and therefore cannot be measured with more bulky measuring devices.

The invention claimed is:

1. A device for making quantified determinations of characteristic parameters of a surface, the characteristic parameters being selected from the group of gloss, haze, and distinctness of image, comprising:
 at least one optical system having:
  a light diode emitting an emitted light at the surface so that said emitted light hits the surface at a predetermined angle of incidence, said emitted light having a light intensity over the entire visible spectral range;
  a lens parallelizing said emitted light before said emitted light hits the surface;
 at least one photo sensor receiving a reflected light from the surface at a predetermined angle of reflection, said photo sensor generating a signal based on said reflected light, wherein said predetermined angle of incidence and said predetermined angle of reflection are mirror symmetrical to each other with respect to a normal to the surface;
 filter means arranged in a light path between said light diode and said at least one photo sensor and for adapting a spectrum such that an aggregate spectrum of said light diode, said at least one photo sensor, and said filter means corresponds to an aggregate of daylight spectrum and eye sensitivity;
 a lens for focusing said reflected light into a light beam, wherein said light beam impinges on said at least one photo sensor; and
 evaluation means for determining the gloss, haze, and distinctness of image of the surface based on said signal, said signal corresponding to portions of said reflected light, wherein said at least one optical system comprises three optical systems, and wherein said predetermined angle of incidence and reflection is different for each of said three optical systems.

2. The device according to claim 1, wherein said predetermined angles of incidence and reflection angles selected from the group consisting of 0°, 10°, 15°, 20°, 30°, 45°, 60°, 75°, 80°, and 85°.

3. The device according to claim 1, wherein said emitted light comprises at least one light strip.

4. The device according to claim 1, further comprising a temperature device for determining a temperature of each of said light diode and said at least one photo sensor so that a temperature-corrected determination of characteristic parameters can be made.

5. The device according to claim 1, further comprising a measurement wheel positionable on the surface to maintain a constant spacing therefrom during movement of the device relative to the surface.

6. The device according to claim 1, wherein said at least one photo sensor comprises at least three photo sensitive elements.

7. The device according to claim 1, further comprising a measurement cycle of less than 0.2 seconds.

8. The device according to claim 1, wherein said light diode comprises a light emitting member, said light emitting member having a precisely defined position within the light diode, wherein said precisely defined position does not vary over time.

9. The device according to claim 1, wherein each of said predetermined angles of incidence do not vary over time.

10. The device according to claim 1, further comprising a scatter disk arrangement positioned with respect to said light diode so that said emitted light homogeneously illuminates the surface.

11. The device according to claim 1, wherein said three optical systems are arranged in such a way that all three of said three optical systems essentially illuminate a same measurement point.

12. The device according to claim 1, further comprising a plurality of photo sensors arranged adjacent to one another.

13. The device according to claim 1, wherein at least a portion of said emitted light comprises a light pattern.

14. The device according to claim 13, wherein said light pattern comprises at least one light/dark edge.

15. The device according to claim 13, wherein said light pattern is a pattern selected from the group consisting of a grid form, a cross-mesh form, an ellipse form, and a circular form.

16. A method for making quantified determinations of the gloss, haze, and distinctness of image of a surface, comprising the steps of:
controlling a light diode to emit an emitted light at the surface so that said emitted light hits the surface at a predetermined angle of incidence, said emitted light having a light intensity over the entire visible spectral range;
parallelizing said emitted light before said emitted light hits the surface;
focusing a reflected light that is reflected from the surface along a predetermined angle of reflection into a light beam having an aggregate spectrum, wherein said angle of incidence and said angle of reflection are mirror symmetrical with respect to a normal to the surface;
arranging a photo sensor so that said light beam impinges onto said photo sensor;
controlling said photo sensor to detect said light beam and to emit an electrical signal based on said light beam;
arranging a filter means in a light path between said light diode and said photo sensor, said filter means filtering said emitted light and/or said reflected light so that an aggregate spectra corresponds to an aggregate of daylight spectrum and eye sensitivity;
determining the gloss, haze, and distinctness of image based on said signal, said signal corresponding to portions of said reflected light;
controlling a second light diode to emit a second emitted light at the surface so that said second emitted light hits the surface at a second predetermined angle of incidence, said second emitted light having a light intensity over the entire visible spectral range, said second predetermined angle of incidence being different from said predetermined angle of incidence;
parallelizing said second emitted light before said second emitted light hits the surface;
focusing a second reflected light that is reflected from the surface along a second predetermined angle of reflection into a second light beam having an aggregate spectrum, wherein said second angle of incidence and second angle of reflection are mirror symmetrical with respect to a normal to the surface, said second predetermined angle of reflection being different from said predetermined angle of reflection;
arranging a second photo sensor so that said second light beam impinges onto said second photo sensor;
controlling said second photo sensor to detect said second light beam and to emit a second electrical signal based on said second light beam;
arranging a second filter means in a second light path between said second light diode and said second photo sensor, said second filter means filtering said second emitted light and/or said second reflected light so that an aggregate spectra corresponds to an aggregate of daylight spectrum and eye sensitivity; and
determining the gloss, haze, and distinctness of image based on said signal and said second signal.

17. The method according to claim 16, wherein determining the gloss haze, and distinctness of image comprises a measurement cycle of less than 0.2 seconds.

18. The method according to claim 16, further comprising arranging a plurality of photo sensors adjacent to one another.

19. The method according to claim 16, further comprising causing relative movement between said light diode and said photo sensor and the surface.

20. The method according to claim 16, wherein said light diode comprises a light emitting member, said light emitting member having a precisely defined position within the light diode, wherein said precisely defined position does not vary over time.

21. The method according to claim 16, wherein said angle of incidence does not vary over time.

22. The method according to claim 16, further comprising positioning a scatter disk arrangement with respect to said light diode so that said emitted light homogeneously illuminates the surface.

23. The method according to claim 16, further comprising causing at least a portion of said emitted light to comprise a light pattern.

24. The method according to claim 23, wherein said light pattern comprises at least one light/dark edge.

25. The method according to claim 23, wherein said light pattern is a pattern selected from the group consisting of a grid form, a cross-mesh form, an ellipse form, and a circular form.

* * * * *